United States Patent
Matharu et al.

(10) Patent No.: US 9,657,027 B2
(45) Date of Patent: May 23, 2017

(54) PROCESSES FOR MAKING HYDROCODONE, HYDROMORPHONE AND THEIR DERIVATIVES

(71) Applicant: Johnson Matthey Public Limited Company, London (GB)

(72) Inventors: Saroop Singh Matharu, Shirley, MA (US); Ewart Grant, Woburn, MA (US); Brian W. Heinrich, Fitchburg, MA (US)

(73) Assignee: Johnson Matthey Public Limited Company, London (GB)

( * ) Notice: Subject to any disclaimer, the term of this patent is extended or adjusted under 35 U.S.C. 154(b) by 0 days.

(21) Appl. No.: 15/004,369

(22) Filed: Jan. 22, 2016

(65) Prior Publication Data

US 2016/0137655 A1    May 19, 2016

Related U.S. Application Data (62) Division of application No. 14/197,242, filed on Mar. 5, 2014, now Pat. No. 9,273,060.

(51) Int. Cl.
| | | |
|---|---|---|
| *C07D 489/02* | (2006.01) | |
| *A61K 31/485* | (2006.01) | |
| *C07D 489/04* | (2006.01) | |

(52) U.S. Cl.
CPC ......... *C07D 489/02* (2013.01); *C07D 489/04* (2013.01)

(58) Field of Classification Search
CPC ............................ C07D 489/02; A61K 31/485
USPC ...................................... 546/44, 45; 514/282
See application file for complete search history.

(56) References Cited

U.S. PATENT DOCUMENTS

| | | |
|---|---|---|
| 3,812,132 A | 5/1974 | Grew et al. |
| 8,399,671 B2 | 3/2013 | Orr et al. |
| 2006/0009479 A1 | 1/2006 | Bailey et al. |
| 2006/0205752 A1* | 9/2006 | Whitehead .................... 514/282 |

* cited by examiner

*Primary Examiner* — Charanjit Aulakh
(74) *Attorney, Agent, or Firm* — Shanay M. McCastle (57) ABSTRACT

Improved processes for making hydrocodone and hydromorphone as well as their 8,14-dihydrothebaine and 8,14-dihydrooripavine derivatives and salts are disclosed.

20 Claims, 2 Drawing Sheets

PROCESSES FOR MAKING HYDROCODONE, HYDROMORPHONE AND THEIR DERIVATIVES

CROSS-REFERENCE TO RELATED APPLICATIONS

This application is a divisional of U.S. patent application Ser. No. 14/197,242, filed Mar. 5, 2014, the disclosure of which is incorporated herein by reference in its entirety for all purposes.

FIELD OF THE INVENTION

The present disclosure relates to improved processes for making hydrocodone and hydromorphone as well as their derivatives and salts.

BACKGROUND OF THE INVENTION

Hydrocodone and hydromorphone are semi-synthetic opioids. Hydrocodone (a synonym for dihydrocodeinone) is a codeine derivative whereas hydromorphone (a synonym for dihydromorphinone) is a morphine derivative. Historically, hydrocodone, commonly as a bitartrate salt, has been used orally as an antitussive or as a narcotic analgesic for treating moderate to severe pain, often in combination with paracetamol (acetaminophen) or ibuprofen. It is approximately 1.5 times less potent an opioid than oxycodone. In the United States, hydrocodone, by itself, is a Schedule II drug. Until recently, the only commercial hydrocodone products approved by the U.S. Food and Drug Administration (USFDA) were combined with another medication, which is often a painkiller and is most frequently acetaminophen. These medications, which are classified as Schedule III products, include Anexsia®, Lortab®, Norco® and Zydone®. The rationale of combining hydrocodone with other painkillers is that the combination may increase efficacy and the adverse effects may be reduced as compared with an equally effective dose of a single active agent. Recently, several pharmaceutical companies have been developing extended-release formulations of hydrocodone by itself and, in October 2013, USFDA approved Zohydro™ ER (Zogenix Inc.) which may avoid the issue of hepatotoxicity of acetaminophen containing formulations.

Hydromorphone, commonly as a hydrochloride salt, is also a potent analgesic drug of the opioid class. Like hydrocodone, hydromorphone is also used as an antitussive for cases of dry, painful coughing. Hydromorphone is commonly used in hospital settings, mostly intravenously (IV) because its bioavailability orally, rectally, and intranasally is very low. Sublingual administration is usually superior to swallowing for bioavailability and effects. Hydromorphone is significantly more potent and much more soluble in water than morphine and therefore hydromorphone solutions can be produced to deliver the drug in a smaller volume of water. Hydromorphone is known by various brand names around the world including Dilaudid™, Hydal™, Dimorphone™, Sophidone™, Hydrostat™, Hydromorfan™, Hydromorphan™, Hymorphan™, Laudicon™ and Opidol™.

An extended-release version of hydromorphone called Palladone™ was available for a short time in the United States before being voluntarily withdrawn from the market after a July 2005 USFDA advisory warned of a high overdose potential when taken with alcohol. There is, however, a newer extended-release (once-daily) version of hydromorphone, approved by USFDA in March 2010 and now available in the United States, marketed under the brand name Exalgo® (Mallinckrodt Inc.). It has been reported that Exalgo® does not have the same "dose dumping" issue as Palladone™. An identical once-daily formulation has been launched in several countries under the trade name Jurnista® (Janssen-Cilag). Exalgo® and Jurnista® both employ the Oros® Push-Pull™ osmotic delivery system designed to release hydromorphone at a controlled rate over an extended period of time allowing for once-daily administration. Like hydrocodone, and the other opioids used for analgesia, hydromorphone is classified as a Schedule II drug in the United States.

Conventional processes for making hydrocodone and hydromorphone involve the use of codeine and morphine, respectively, as starting materials and oxidation/reduction steps. However, these processes are generally considered to be more expensive and less efficient than known "diimide" routes to making hydrocodone and hydromorphone from thebaine and oripavine, respectively.

A process for preparing hydrocodone from thebaine by reducing thebaine to 8,14-dihydrothebaine with diimide, followed by hydrolysis of the 8,14-dihydrothebaine to hydrocodone, is described in U.S. Pat. Nos. 3,812,132 and 8,399,671 (incorporated herein by reference in their entirety). Similarly, a process for preparing hydromorphone from oripavine by reducing the oripavine to 8,14-dihydroripavine with diimide, followed by hydrolysis of the 8,14-dihydroripavine to hydromorphone is also described in U.S. Pat. No. 8,399,671 as well as U.S. Pat. Appl. Publ. No. 2006/0009479.

These known processes provide for the formation of diimide in situ by heating a sulfonic acid hydrazide, such as p-toluenesulfonyl hydrazide, in an organic solvent, with or without the presence of a base such as an alkali metal hydroxide or an organic base such as ethanolamine or morpholine.

Contacting the heated sulfonic acid hydrazide and solvent with a thebaine or oripavine solution results in the evolution of gases, such as nitrogen, that are bi-products of the processes. The potential exists for these gases to increase in volumn and pressure, and therefore can pose safety issues especially when the hydrazide is added rapidly to the thebaine and oripavine solutions. Additionally, isolation of the 8,14-dihydrothebaine or 8,14-dihydroripavine products typically involves a tedious solvent distillation at the end of the reaction, followed by the addition of water and basification. The distillation process can result in product impurities either from the residual hydrazide reagent or from degradation of by-products of the process.

As with other pharmaceutical processes, it is desirable to attain improvements especially with respect to process safety and product impurities. In particular, there is a continuing need in the art to provide improved processes for making hydrocodone and hydromorphone alkaloids. We have discovered improved processes for making hydrocodone and hydromorphone as well as their derivatives 8,14-dihydrothebaine and 8,14-dihydrooripavine.

All references cited herein are incorporated by reference in their entireties for all purposes.

SUMMARY OF THE INVENTION

It is an object of certain embodiments of the present invention to provide a process for more safely making hydrocodone, hydromorphone and their derivatives and salts.

It is also an object of certain embodiments of the present invention to provide a more effecient process for more making hydrocodone, hydromorphone and their derivatives and salts.

It is a further object of certain embodiments of the present invention to provide a process for making hydrocodone, hydromorphone and their derivatives and salts which is more easily controlled.

It is still further an object of certain embodiments of the present invention to provide a more cost-effective process for more making hydrocodone, hydromorphone and their derivatives and salts.

Additionally, it is an object of certain embodiments of the present invention to provide a process for making hydrocodone, hydromorphone and their derivatives and salts which allows for the improved isolation of products.

Moreover, it is an object of certain embodiments of the present invention to provide a process for making hydrocodone, hydromorphone and their derivatives and salts which results in highly pure products.

In certain embodiments, the invention is directed to a process for preparing 8,14-dihydrothebaine by adding a sulfonic acid hydrazide base solution to a thebaine/solvent mixture to form the 8,14-dihydrothebaine.

Additionally, in certain embodiments of the present invention, the amount and/or rate of addition of the sulfonic acid hydrazide reagent is controlled in order to minimize the rate at which bi-product gases are emitted from the reaction mixture. Controlling the addition of the sulfonic acid hydrazide also improves the control of diimide as it is consumed during its reaction with thebaine to produce 8,14-dihydrothebaine and as it decomposes to nitrogen and hydrogen/hydrazine. Preferably, the amount of the sulfonic acid hydrazide reagent added to the reaction mixture is about 2 equivalents, more preferably, 2.0 equivalents.

Similarly, in certain other embodiments, the invention is directed to a process for preparing 8,14-dihydroripavine by adding a sulfonic acid hydrazide base solution to a oripavine/solvent mixture to form the 8,14-dihydrooripavine. Again, in certain embodiments of the present invention, the addition of the sulfonic acid hydrazide reagent is controlled in order to minimize the rate at which bi-product gases are emitted from the reaction mixture.

In certain embodiments, the invention is directed to a process for preparing hydrocodone by first preparing 8,14-dihydrothebaine by a process described in this application and then hydrolyzing the 8,14-dihydrothebaine to form hydrocodone.

Similarly, in certain other embodiments, the invention is directed to a process for preparing hydromorphone by first preparing 8,14-dihydroripavine by a process described herein and then hydrolyzing the 8,14-dihydrooripavine to form hydromorphone.

In certain embodiments, the hydrocodone and hydromorphone preparations are converted to various salts including, for example, hydrocodone bitartrate and hydromorphone hydrochloride. The hydrocodone and hydromorphone preparations, including their salt forms, can be, for example, a hydrocodone active pharmaceutical ingredient (API) or a hydromorphone API such as hydrocodone bitartrate U.S.P. and hydromorphone hydrochloride U.S.P., respectively. These APIs can be combined with other ingredients including excipients or other APIs to form final pharmaceutical dosage forms.

DETAILED DESCRIPTION OF THE INVENTION

Surprisingly, applicants have been able to overcome the issues described above that are the result of the in situ formation of a diimide when either thebaine or oripavine is contacted with a sulfonic acid hydrazide. More specifically, the process of the present invention is more easily controlled at least from the standpoint that the diimide reaction rate is controlled by the rate of addition of a hydrazide solution and by maintaining the reaction temperature. Other advantages include a more efficient process compared to those known in the art at least from the standpoint that solvent distillation and aqueous basification steps are not required. The avoidance of these steps also allows for improved product isolation as impurity formation is less likely to occur. The present invention also tends to be more cost effective compared to coventional methods of making hydrocodone and hydromorphone which use relatively expensive and valuable codeine and morphine starting materials and involve two or more processes such as reduction/oxidation or metal catalyzed rearrangement. Accordingly, the present invention provides a safer, as well as a more efficient and cost-effective, process for making hydrocodone and hydromorphone as well as their derivatives and salts.

The sulfonic acid hydrazide may be, for example, an aryl sulfonic acid hydrazide in which the aryl group is a benzene or naphthalene that can be mono or poly alkyl substituted. Alternatively, the sulfonic acid hydrazide may be an alkyl sulfonic acid hydrazide such as methane sulfonic hydrazide or others with branched or unbranched alkyl groups (see, e.g., U.S. Pat. No. 3,182,132). Preferably, the sulfonic acid hydrazide is p-toluenesufonyl hydrazide.

In certain embodiments, the invention is directed to a process for preparing 8,14-dihydrothebaine by combining a sulfonic acid hydrazide base solution with a thebaine mixture to form the 8,14-dihydrothebaine. In these embodiments, thebaine is at least partially dissolved in an alkoxy solvent to form a thebaine mixture.

Thermal screening experiments have shown that p-toluenesulfonylhydrazide decomposes at about 110° C. to produce diimide. When heated in the presence of ethanolamine, this decomposition begins at a lower temperature (e.g., about 75° C.). Applicants have discovered that, preferably, the thebaine mixture is heated to a temperature of 108±10° C., most preferably to 108±2° C. as this temperature range is below the boiling point of the alkoxy solvent and ensures complete decomposition of p-toluenesulfonylhydrazide to produce diimide.

Separately, a sulfonic acid hydrazide, preferably p-toluenesulfonylhydrazide is dissolved in an organic base to form a hydrazide base solution. The hydrazide base solution is combined with the thebaine mixture to form a reaction mixture that is cooled to precipitate 8,14-dihydrothebaine. Preferably, the hydrazide base solution is added to the thebaine mixture and, most preferably, the addition occurs continuously at a steady rate (e.g., 2 liters/minute on a 100 Kg scale) in order to avoid vigorous evolution of the gaseous by-products, such as nitrogen. Reaction calorimetry has demonstrated that addition of p-toluenesulfonyl hydrazide by this procedure does not produce a large exotherm and is easy to control by external cooling. Alternatively the addition of the solution of the p-toluenesulfonyl hydrazide reagent can be performed in several portions to avoid vigorous evolution of the gaseous by-products and the reaction exotherm controlled by the size of each addition.

Similarly, in certain embodiments, the invention is directed to a process for preparing 8,14-dihydrooripavine by combining a sulfonic acid hydrazide base solution with a oripavine mixture to precipitate the 8,14-dihydrooripavine. In these embodiments, oripavine is at least partially dissolved in an alkoxy solvent and the resulting oripavine mixture is heated, preferrably to a temperature of 108±10° C. and, most preferably, to 108±2° C. Separately, a sulfonic acid hydrazide is dissolved in an organic base after which the resulting hydrazide base solution is combined with the oripavine mixture to form a reaction mixture that is cooled to precipitate 8,14-dihydrooripavine. Preferably, the hydrazide base solution is added to the oripavine mixture and, most preferably, the addition occurs continuously at a steady rate.

Preferably, the alkoxy solvent is an alkoxy alkanol or an alkoxy alkandiol, non-limiting examples of which include 2-methoxyethanol, 2-ethoxyethanol, 2-propoxyethanol, 1-methoxy-2-propanol, 1-methoxy-2-butanol, 3-methoxy-1-butanol, 3-methoxy-3-methyl-1-butanol and 3-methoxy-1,2-propandiol. Preferably, the alkoxy solvent is selected from 2-methoxyethanol, 2-ethoxyethanol, 2-propoxyethanol, 1-methoxy-2-propanol, 1-methoxy-2-butanol, 3-methoxy-1-butanol, 3-methoxy-3-methyl-1-butanol and 3-methoxy-1,2-propandiol and, most preferably, is 1-methoxy-2-propanol, Similar to an ethereal solvent, thebaine and oripavine both dissolve in the alkoxy alkanol or alkoxy alkandiol group of solvents including those specifically described above. These solvents are also water-miscible which enables the precipitated 8,14-dihydrothebaine and 8,14-dihydrooripavine products to be more easily isolated. The 8,14-dihydrothebaine and 8,14-dihydrooripavine products are more easily isolated by adding water to the reaction mixture and filtering either the 8,14-dihydrothebaine product or the or 8,14-dihydrooripavine products.

In certain embodiments, the sulfonic acid hydrazide is dissolved, at ambient temperature, in excess organic base. It is preferred that the organic base is present in an amount that is about 12 equivalents relative to thebaine or oripavine as this excess amount of organic base provides for easy combination of the hydrazide base solution with the thebaine mixture or oripavine mixture. It is further preferred that the organic base is ethanoamine, morpholine, ethylenediamine or 1,3-propanediamine, most preferably ethanoamine. Similar to the preferred alkoxy solvents described above, these organic bases are water-miscible and thus their use is advantageous in isolating the 8,14-dihydrothebaine or 8,14-dihydrooripavine products. An additional advantage of using excess organic base is that, after the addition of water to isolate the 8,14-dihydrothebaine and 8,14-dihydrooripavine products, the resulting mixture is sufficiently basic (e.g., pH>9,5) such that the products precipitate out of solution in the free base form. As a result, the need for additional base, such as caustic soda, is avoided.

Yet an additional advantage of using excess organic base is that, after the addition of water to isolate the 8,14-dihydrothebaine and 8,14-dihydrooripavine products, the sulfinic acid by-product from the decomposition of the sulfonic acid hydrazide are present as water soluble organic base salts and as such are easily removed from the product during its filtration. For example, during the preparation of 8,14-dihydrothebaine when p-toluenesulfonyl hydrazide is used in presence of ethanolamine, the reaction by-product p-toulenesulfinic acid is removed as the water-soluble ethanolamine salt during filtration of the solid product.

In certain embodiments, the processes for preparing 8,14-dihydrothebaine and 8,14-dihydrooripavine include combining a co-solvent with the alkoxy solvent. In these instances, preferably, the co-solvent is an organic base, most preferably, ethanolamine, morpholine, ethylenediamine, or 1,3-propanediamine. Similarly, in certain embodiments, the processes for preparing 8,14-dihydrothebaine and 8,14-dihydrooripavine include combining a co-solvent with the organic base solution. In these instances, the co-solvent is preferably an alkoxy alkanol or an alkoxy alkandiol, most preferably, 2-methoxyethanol, 2-ethoxyethanol, 2-propoxyethanol, 1-methoxy-2-propanol, 1-methoxy-2-butanol, 3-methoxy-1-butanol, 3-methoxy-3-methyl-1-butanol or 3-methoxy-1,2-propandiol. It is preferable to combine a co-solvent with the alkoxy solvent and, separately, a co-solvent with the organic base as doing so facilitates the formation of a solution; however, both of these co-solvent combinations are optional.

The yield of the 8,14-dihydrothebaine and 8,14-dihydrooripavine products is expected to be typically about 90% (range 70% to 99%) and the area % purity of the products by HPLC analysis is expected to be about 99% (range 97% to 99%).

As set forth above, hydrocodone and hydromorphone, as well as their salts, are well known opioid compounds that have been, and continue to be, used as active ingredients in a variety of pharmaceutical products. In certain other embodiments, the present invention is directed to processes for preparing hydrocodone base and hydromorphone base by first preparing 8,14-dihydrothebaine and 8,14-dihydrooripavine, respectively, by the processes described herein and then hydrolyzing the 8,14-dihydrothebaine and 8,14-dihydroripavine to form hydromorphone and hydromorphone. The hydrolyzing step for converting 8,14-dihydrothebaine and 8,14-dihydroripavine to hydromorphone and hydromorphone, respectively, is known in the art. See, for example, Examples 4-8 of U.S. Pat. No. 8,399,671. Generally, the hydrolyzing step includes mixing, e.g., 8,14-dihydrothebaine with a concentrated acid (e.g., 2-12 N HCl), stirring the mixture for several hours, cooling the mixture as needed, increasing the pH (e.g., ≈9.5) of the mixture by adding a base (e.g., $NH_4OH$) to precipiate the hydrocodone base product, filtering and drying the product. A similar hydrolysis procedure is set forth in U.S. Pat. No. 3,812,132 starting at column 3, line 70.

In certain other embodiments, the present invention is directed to processes for converting hydrocodone base and hydromorphone base into physiologically-tolerable salt forms, such as the hydrocodone bitartrate and hydromorphone hydrochloride, using methods known to those of skill in the art.

The following examples illustrate various aspects of the present invention. Those skilled in the art will recognize many variations that are within the spirit of the invention and scope of the claims. As such, the examples are not to be construed to limit the claims in any manner whatsoever.

Starting Materials: Thebaine and Oripavine

Any starting materials comprising thebaine or oripavine may be used to carry out the present invention. Alkaloids, including thebaine or oripavine, are extracted from the poppy capsules of Papaver somniferum by two commercial methods. In one method, the immature capsule is cut and the latex collected from the wound. The air-dried latex is opium which, according to the Merck Index, 11th edition, contains alkaloids in the amounts shown in Table 1. In a second method, the mature poppy capsules and the poppy capsule stems are collected. and threshed to remove the seeds and form a straw. When necessary, the straw is dried to a water content below 16%. Solvent or water extraction is employed to remove the alkaloids from the straw. For the varieties of Papaver somniferum normally grown, the straw, on a dry basis, contains alkaloids in the amounts shown in Table 1.

TABLE 1

|  | opium | straw |
|---|---|---|
| morphine, % | 10-16 | 1-3 |
| codeine, % | 0.8-2.5 | 0.05-0.3 |
| oripavine, % | 0-0.1 | 0-0.05 |
| thebaine, % | 0.5-2 | 0.15-0.65 |

As can be seen, the yield of thebaine and oripavine is confounded with that of other alkaloids. A poppy producing predominantly thebaine, e.g., as 90% or more of the total alkaloids, would enable a simpler extraction¡purification process, resulting in higher yields, better quality and throughput and lower costs.

Where solvent or water or super critical fluid, such as $CO_2$, extraction is employed to remove the alkaloids from the straw, such method, as practiced, involves the production of "Concentrate of Poppy Straw". Concentrate of Poppy Straw (or "CPS") is described as "The material arising when poppy straw has entered into a process for the concentration of its alkaloids, when such material is made available in trade," (Multilingual dictionary of narcotic drugs and psychotropic substances under international control, United Nations, New York, 1983). Not inconsistent with the foregoing description, Concentrate of Poppy Straw is described as "the crude extract of poppy straw in either liquid, solid or powder form which contains the phenanthrene alkaloids of the opium poppy," 45 U. S. Federal Register 77466, Nov. 24, 1980. When in liquid form, the liquid is preferably concentrated before entering into commerce. The generally preferred Concentrate of Poppy Straw is the powder form which results from removing the solvent or water following extraction of the poppy straw. According to the United Nations publication "Narcotic Drugs: Estimated World Requirements for 2007; Statistics for 2005 (E/INCB/2006/2)", Concentrate of Poppy Straw is the dried residue obtained through the extraction of alkaloids from poppy straw. Until the second half of the 1990s, only concentrate of poppy straw containing morphine as the main alkaloid was manufactured. Since then, concentrate of poppy straw containing mainly thebaine or oripavine has started to be manufactured.

More recently, Fist et al., in U.S. Pat. Nos. 6,067,749 (the "749 Patent"), 6,376,221 and 6,723,894, disclosed an improved poppy straw of a stably reproducing Papaver somniferum for the extraction of thebaine and/or oripavine (the "Norman" poppy), the threshed straw having thebaine and oripavine constituting about 50% by weight or greater of the alkaloid combination consisting of morphine, codeine, thebaine and oripavine. The Norman poppy straw constituted 1.68% thebaine, 0.74% oripavine, 0.05% codeine and no morphine as a percent by weight of the dry straw. (See, column 15, table III of the 749 Patent). While this alleviated the limited availability and high cost of thebaine to some extent, the problem of producing oripavine concurrently with thebaine contributed sianificantly to the cost of producing thebaine. For many years, the perennial poppy Papaver bracteatum has been proposed as a source of thebaine. Thebaine is the predominant alkaloid in this species, and in selected strains it can be as high as 98% of the total alkaloids (Palevitch, D and Levy, A 1992 Acta Horticulturae 306, 33-52). Thebaine is present in the roots as well as capsules. Generally two years of growth would be required to obtain a good yield of both roots and capsules. Papaver bracteatum does not alleviate the problem of limited availability and high cost of thebaine because of its slow growth, low capsule yield and the problems with harvesting and processing roots.

Preferably, the starting materials are purified thebaine and purified oripavine, or a concentrate of poppy straw comprising thebaine as the main alkaloid (CPS-T) and a concentrate of poppy straw comprising oripavine as the main alkaloid (CPS-O).

HPLC Analytical Method

Related Substances (HPLC):

Hydrocodone: NMT 0.15% w/w for thebaine, 8,14 dihydrothebaine, p-toluenesulfinate, p-toluenesulfonate, p-toluenesulfonyl hydrazide, s-(p-tolyl) p-toluenethiosulfonate, NMT 0.10% area for unspecified impurities.

Hydromorphone: NMT 0.15% w/w for oripavine, 8,14 dihydrooripavine, p-toluenesulfinate, p-toluenesulfonate, p-toluenesulfonyl hydrazide, s-(p-tolyl) p-toluenethiosulfonate, NMT 0.10% area for unspecified impurities.

Reagents and Materials: (Equivalent reagents and materials may be substituted)

For Hydrocodone

| | |
|---|---|
| Potassium Phosphate Dibasic ($K_2HPO_4$) | Aldrich, Reagent Grade, 99% |
| Methanol (MeOH) | Thermo Fisher Scientific, HPLC Grade |
| 8,14-Dihydrothebaine | JM Reference Standard Candidate |
| Thebaine | JM Qualified Reference Standard |
| Hydrocodone Bitartrate | JM Qualified Reference Standard |
| Sodium p-toluenesulfinate | Aldrich, 95% |
| p-Toluenesulfonic Acid Monohydrate | Aldrich, 98.5% |
| p-Toluenesulfonyl Hydrazide | Aldrich, 97% |
| s-(p-Tolyl) p-Toluenethiosulfonate | Aldirch, the purity was not specified |
| Purified Water ($H_2O$) | MilliQ, Model A10 Gradient Water System |

For Hydromorphone

| | |
|---|---|
| Potassium Phosphate Dibasic ($K_2HPO_4$) | Aldrich, Reagent Grade, 99% |
| Methanol (MeOH) | Thermo Fisher Scientific, HPLC Grade |
| 8,14-Dihydrooripavine | JM Reference Standard Candidate |
| Oripavine | JM Qualified Reference Standard |
| Hydromorphone Hydrochloride | JM Qualified Reference Standard |
| Sodium p-toluenesulfinate | Aldrich, 95% |
| p-Toluenesulfonic Acid Monohydrate | Aldrich, 98.5% |
| p-Toluenesulfonyl Hydrazide | Aldrich, 97% |
| s-(p-Tolyl) p-Toluenethiosulfonate | Aldrich, the purity was not specified |
| Purified Water ($H_2O$) | MilliQ, Model A10 Gradient Water System |

Instrumentation: (Equivalent nstrumentation can be used)

| | |
|---|---|
| UPLC | Waters Alliance HPLC System with Column Heater |
| UV Detector | Waters 2487 Dual Wavelength Detector |
| Data System | Chromatography Data System, Current JM Version |

-continued

| | |
|---|---|
| Balance | Mettler-Toledo, Model AT261 or PG503-S, Delta Range |
| pH Meter | Beckman, Model 320 |

Mobile Phase Preparation: (For 1 L each)
Mobile Phase A: Transfer 900 mol of deionizer water into a suitable mobile phase container, weigh 5.0 g of Potassium Phosphate dibasic and transfer into the mobile phase container, shake and sonic ate to dissolve completely. Transfer 100 mol of MeOH into the container, mix well, and degas under vacuum for 10 min.
Mobile Phase B: Transfer 1000 mL of MeOH into a suitable mobile phase container and degas under vacuum for 10 min.
Diluent: 50% MeOH in water.
Operating Conditions:

| LC Conditions | |
|---|---|
| Column | Waters, Xbridge $C_{18}$, 3.5 µm, 150 × 4.6 mm |
| Col. Temperature | 35° C. |
| Sample Temperature | Ambient |
| Injection Volume | 10 µL |
| Detection | UV at 220 nm |
| Flow Rate | 0.8 mL/min |

| Gradient Conditions | | | |
|---|---|---|---|
| Time (min) | % MP A | % MP B | Curve |
| initial | 75 | 25 | — |
| 20 | 20 | 80 | 6 |
| 21 | 10 | 90 | 6 |
| 25 | 10 | 90 | 6 |
| 26 | 75 | 25 | 6 |
| 35 | 75 | 25 | 6 |

Approximate Retention Times of Known Analytes:
For Hydrocodone:

| Analyte | Approx. Retention Time (min) | Approx. RRT |
|---|---|---|
| p-Toluenesulfonate | 3.3 | 0.30 |
| p-Toluenesulfinate | 4.2 | 0.38 |
| p-Toluenesulfonyl Hydrazide | 4.7 | 0.42 |
| Hydrocodone | 11.1 | 1.00 |
| Thebaine | 13.9 | 1.25 |
| 6b-Tetrahydrothebaine | 14.1 | 1.27 |
| 6,7-Dihydrothebaine | 14.6 | 1.32 |
| 8,14-Dihydrothebaine | 14.8 | 1.33 |
| 6a-Tetrahydrothebaine | 15.8 | 1.42 |
| s-(p-Tolyl) p-Toluenethiosulfonate | 18.4 | 1.66 |

For Hydromorphone:

| Analyte | Approx. Retention Time (min) | Approx. RRT |
|---|---|---|
| p-Toluenesulfonate | 3.3 | 0.48 |
| p-Toluenesulfinate | 4.2 | 0.61 |
| p-Toluenesulfonyl Hydrazide | 4.7 | 0.68 |
| Hydromorphone | 6.9 | 1.00 |
| Oripavine | 9.5 | 1.38 |
| 8,14-Dihydrooripavine | 10.3 | 1.49 |
| s-(p-Tolyl) p-Toluenethiosulfonate | 18.4 | 1.66 |

Impurity Working Standard Solution Preparation:
Weigh 30 mg (±3 mg) (accurate to the second digit passed the decimal point) each of the impurity reference standards into a 200 mol volumetric flask. Dissolve and dilute to volume with the diluent. Mix the solution well. This is the impurity stock solution.
Transfer 1.0 mol of the impurity stock solution into a 200 mol volumetric flask, dilute to volume with the diluent, and mix well. This is the impurity standard solution. Keep both solutions in a refrigerator if they are not immediately used.
Sensitivity Check Solution:
Transfer 5 mol of the working standard solution into a 10 mol volumetric flask, dilute to volume with the diluent, and mix well. Keep the solution in a refrigerator if it is not immediately used.
Sample Solution Preparation:
In duplicate, accurately weigh 25 mg (±2 mg) of the sample into a 50 mol volumetric flask. Add ~30 mol of the diluent, vortex, sonic ate with tapping to dissolve completely, dilute to volume with the diluent, and mix well.
System Equilibration and Conditioning:
Pump Mobile Phase B for at least 30 minutes at a flow rate of 0.8 mol/min. Switch to Initial assay conditions and pump for at least 30 minutes.
Procedure:
Inject the diluent as a blank.
Inject the sensitivity check solution once.
Inject three times of the impurity working standard solution.
Ensure that the system suitability criteria are met.
Inject each sample solution in duplicate under the full gradient profile.
Inject two injections of the working standard solution as the standard check at the end of all sample injections.
Inject the diluent at the end.
Ensure that the results of the standard check are satisfied.
Quantify the specified impurities in each sample by comparing the averaged peak area to the averaged response among the five injections of the working standard solution.
Integrate all peaks larger than 0.01% area and report % area and RRT of unspecified impurity(s).
System Suitability:
Sensitivity: The peak height of each specified impurity in the sensitivity check solution must be NLT ten (10) times the noise height at the same retention time in the diluent injection (Noise level determination: the baseline of the diluent injection is integrated in three segments at the approximately same retention time as the impurity in the sensitivity check solution. The noise level is the averaged peak height of the three segments).

Precision: The % RSD of each specified impurity peak area responses, from three injections of the working standard solution, must be NMT 10.0%.

Standard Check: The % difference between each specified impurity averaged peak area (used as the denominator in the calculation) of the three working standard solution injections and the same impurity averaged peak area of the two standard check injections must be NMT 10.0%.

Calculations:

Specified Impurity:

$$\% \text{ w/w} = \frac{(Imp \text{ Std}^{Conc. \text{ mg/mL}})(Imp \text{ Std Purity\{in decimal\}})}{(Imp \text{ Std}^{Avg \text{ PA}})(Sample^{Conc. \text{ mg/mL}})}$$

where:

| | |
|---|---|
| Imp = | Impurity |
| PA = | Peak Area |
| Std = | Standard |
| Avg = | Average |
| Conc = | Concentration (mg/mL) |

Unspecified Impurity:

$$\% \text{ area} = \frac{Imp \text{ } PA \times 100}{\text{Total Peak Area (disregard peaks in the blank)}}.$$

EXAMPLE 1

(Conversion of Thebaine to 8,14-Dihydrothebaine (Examples 1 to 9))

Figure 1:
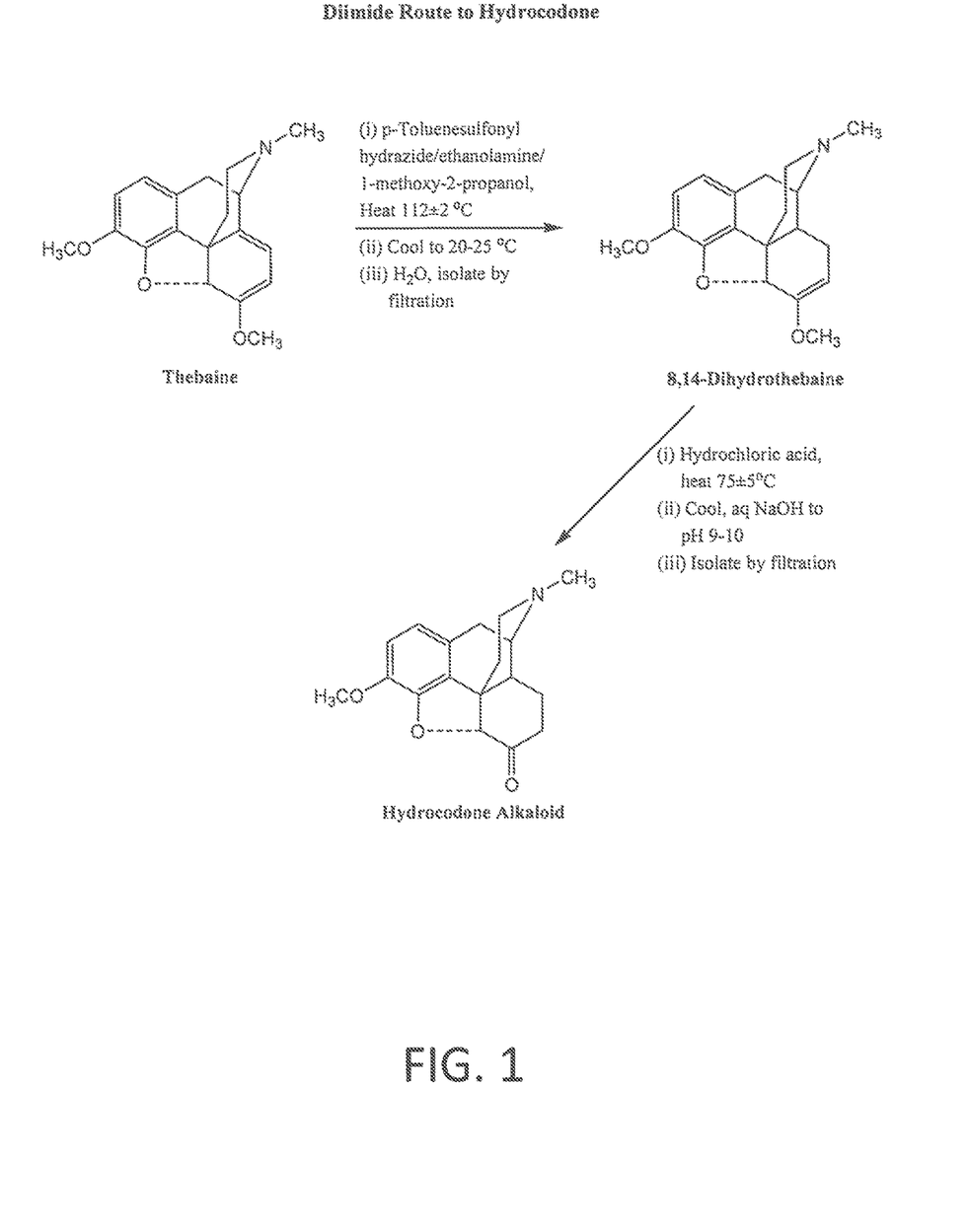
FIG. 1 is a schematic of a reaction of thebaine to hydrocodone alkaloid via 8,14-dihydrothebaine according to an embodiment of the present invention.

Thebaine (500.0 g containing 24.4 wt % water, 378.0 g dry basis, 1.21 mol, 1.0 equiv) is placed in a mixture of 1-methoxy-2-propanol (1304.2 g) and ethanolamine (130.6 g, 2.13 mol, 1.76 equiv) and is heated to 108±2° C. to give almost a complete solution. In another vessel, p-toluenesulfonylhydrazide (PTSH) (480.0 g, 2.57 mol, 2.12 equiv) is dissolved in a mixture of ethanolamine (960.1 g, 15.72 mol, 13.0 equiv) and 1-methoxy-2-propanol (80.1 g) and held at 20-25° C. The PTSH solution is then added slowly to the thebaine mixture at such a rate that the batch temperature remains in the range 108±2° C. and the gas evolution vents safely. After the complete addition, the reaction mixture is allowed to agitate at 108±2° C. and is monitored for reaction completion (≤0.3 area % thebaine remaining) by in-process HPLC analysis. On completion, the batch is cooled to 15±5° C. Water (1200 g) is then charged to the batch while maintaining the batch temperature at ≤30° C. The resulting slurry is stirred and further cooled to 5±3° C. and held for a minimum of 0.5 to 1 hours. The product is collected by filtration, washed with water (2400 g) and then dried at 55±5° C. to a constant weight to give 8,14-dihydrothebaine (yield, 348.4 g, 91.6% yield; purity, 99.2 area % by HPLC). The process described here in Example 1 is shown schematically in FIG. 1.

EXAMPLE 2

Thebaine (4.0 g dry basis, 12.9 mmol) is placed in a mixture of 1-methoxy-2-propanol (13.0 g) and ethanolamine (1.3 g, 21.3 mmol, 1.65 equiv) and is heated to 110° C. In anther vessel, p-toluenesulfonylhydrazide (4.8 g, 25.8 mmol, 2.0 equiv) is dissolved at room temperature in a mixture of ethanolamine (9.6g, 157.2 mol, 12.2 equiv) and 1-methoxy-2-propanol (0.8 g) and the solution is added in portions to the thebaine mixture over about a 2 hour period while maintaining the batch temperature at ~110° C. The reaction mixture is held at 110 to 112° C. for 1 hour then cooled to 22° C. and water (24 g) added while maintaining the batch temperature at ≤30° C. The resulting slurry (pH 10.8) is filtered and the product is washed with water (3×8 g) and dried at 40° C. to constant weight to give 8,14-dihydrothebaine (3.63 g, 90.1% yield; 98.8 area% purity by HPLC).

EXAMPLE 3

Thebaine (4.0 g dry basis, 12.9 mmol) is placed in a mixture of 1-methoxy-2-propanol (13.0 g) and ethylenediamine (1.3 g, 21.6 mmol, 1.68 equiv) and is heated to 110° C. p-Toluenesulfonylhydrazide (4.8 g, 25.8 mmol, 2.0 equiv) is dissolved at room temperature in a mixture of ethylenediamine (9.6 g, 159.7 mol, 12.4 equiv) and 1-methoxy-2-propanol (0.8 g) and the solution is added in portions to the thebaine mixture over 1 hour 20 minutes at such a rate that the batch temperature is maintained at ~110° C. The reaction mixture is held at this temperature for 1 hour then cooled to room temperature and then water (24 g) is added while maintaining the batch temperature at ≤30° C. The resulting slurry (pH 11.4) is filtered and the product is washed with water (3×8 g) and dried at 40° C. to a constant weight to give 8,14-dihydrothebaine (3.68 g, 91.3% yield; 99.1 area % purity by HPLC).

EXAMPLE 4

Thebaine (4.0 g dry basis, 12.9 mmol) is placed in a mixture of 2-methoxyethanol (13.0 g) and ethanolamine (1.3 g, 21.3 mmol, 1.65 equiv) and is heated at 110 to 114° C., p-Toluenesulfonylhydrazide (4.8 g, 25.8 mmol, 2.0 equiv) is dissolved at 15 to 25° C. in a mixture of ethanolamine (9.6g, 157.2 mol, 12.2 equiv) and 2-methoxyethanol (0.8 g) and then the solution is added in portions to the thebaine mixture at such a rate that the batch temperature is maintained in the range 110 to 115° C. The reaction mixture is held at 110 to 114° C. for 1 hour then cooled to less than 20° C. after which water (24 g) is added to the mixture. The resulting slurry (pH 10.9) is stirred, further cooled to 0 to 5° C. and then filtered. The product is washed with water (3×8 g) and dried at 40° C. to constant weight to give 8,14-dihydrothebaine (3.84 g, 95.3% yield; 98.4 area% purity by HPLC).

EXAMPLE 5

Thebaine (4.0 g dry basis, 12.9 mmol) in mixture of 2-ethoxyethanol (13.0 g) and ethanolamine (1.3g, 21.3 mmol, 1.65 equiv) and is heated to 110 to 114° C. p-Toluenesulfonyhydrazide (4.8 g, 25.8 mmol, 2.0 equiv) is dissolved at 15 to 25° C. in a mixture of ethanolamine (9.6 g, 157.2 mol, 12.2 equiv) and 2-ethoxyethanol (0.8 g) and the solution is added in portions to the thebaine mixture over 1 hour 10 minutes while maintaining the batch temperature in the range 110 to 118° C. The reaction mixture is held at 110 to 114° C. for 1.5 h then cooled to 19° C. and water (24 g) added in two portions while maintaining the batch temperature at ≤30° C. The resulting slurry (pH 10.9) is stirred and further cooled to 0 to 5° C. and then filtered. The product washed with water (3×8 g) and dried at 40° C. to a constant weight to give 8,14-dihydrothebaine (3.64 g, 90.3% yield; 98.5 area % purity by HPLC).

EXAMPLE 6

Thebaine (4.0 g dry basis, 12.9 mmol) is placed in a mixture of 1-methoxy-2-propanol (13.0 g) and morpholine (1.3 g, 14.9 mmol, 1.16 equiv) and is heated at 110 to 114° C. p-Toluenesulfonylhydrazide (4.8 g, 25.8 mmol, 2.0 equiv) is dissolved at 15 to 25° C. in a mixture of morpholine (9.6 g, 110.2 mmol, 8.54 equiv) and 1-methoxy-2-propanol (0.8 g) and the solution added in portions to the Thebaine mixture over 1 h 10 min while maintaining the batch temperature in the range 110 to 115° C. The reaction mixture is held at 110 to 114° C. for 1.75 h then cooled to less than 20° C. and water (24 g) added. The resulting slurry (pH 9.7) is stirred and further cooled to 0 to 5° C. and then filtered. The product is washed with water (3×8 g) and dried at 40° C. to a constant weight to give 8,14-dihydrothebaine (3.59 g, 89.1% yield; 98.7 area % purity by HPLC).

EXAMPLE 7

Thebaine (4.0 g dry basis, 12.9 mmol) is placed in mixture of 1-methoxy-2-butanol (13.0 g) and ethanolamine (1.3 g, 21.3 mmol, 1.65 equiv) is heated at 110 to 114° C. p-Toluenesulfonylhydrazide (4.8 g, 25.8 mmol, 2.0 equiv) is dissolved at 15 to 25° C. in a mixture of ethanolamine (9.6 g, 157.2 mol, 12.2 equiv) and 1-methoxy-2-butanol (0.8 g) and the solution added in portions to the Thebaine mixture over 1 h 10 min. The reaction mixture is held at 110 to 114° C. for 1 h then cooled to 15 to 25° C. and water (24 g) added while maintaining the batch temperature at ≤30° C. The resulting slurry (pH 11.0) is stirred, further cooled to 0 to 5° C. and then filtered. The product is washed with water (3×8 g) and dried at 40° C. to a constant weight to give 8,14-dihydrothebaine (3.87 g, 96.0% yield; 98.3 area % purity by HPLC).

EXAMPLE 8

Thebaine (4,0 g dry basis, 12.9 mmol) is placed in a mixture of 3-methoxy-12-propanediol (13.0 g) and ethanolamine (1.3 g, 21.3 mmol, 1.65 equiv) and is heated at 110 to 114° C. p-Toluenesulfonylhydrazide (4.8 g, 25.8 mmol, 2.0 equiv) is dissolved at 15 to 25° C. in a mixture of ethanolamine (9.6 g, 157.2 mol, 12.2 equiv) and 3-methoxy-1,2-propanediol (0.8 g) and the solution is added in portions to the thebaine mixture over 1.25 hours. The reaction mixture is held at 110 to 114° C. for 1.25 hours then cooled to 15 to 25° C. and water (24 g) added while maintaining the batch temperature at ≤30° C. The resulting slurry (pH 10.9) is stirred, further cooled to 0 to 5° C. and then filtered. The product is washed with water (3×8 g) and dried at 40° C. to a constant weight to give 8,14-dihydrothebaine (3.26 g, 81.0% yield; 97.0 area% purity by HPLC).

EXAMPLE 9

Thebaine (4.0 g dry basis, 13 mmol) is placed in a mixture of 1-methoxy-2-propanol (13.0 g) and 1,3-propanediamine (1.6 g, 22 mmol, 1.66 equiv) and is heated at 105° C. A solution of p-toluenesulfonylhydrazide (4.8 g, 26 mmol, 2.0 equiv) in 1,3-propanediamine (9.6 g, 130 mmol, 9.96 equiv) is added in portions to the thebaine mixture at such a rate that the batch temperature is maintained in the range 105 to 110° C. The reaction mixture is held at 105 to 110° C. for 1 hour then cooled to room temperature and water (24 g) is added while maintaining the batch temperature at ≤30° C. The resulting slurry is stirred, further cooled to ~2° C. and then filtered. The product is washed with water (3 x 8 g) and dried at 40° C. to a constant weight to give 8,14-dihydrothebaine (3.80 g, 94.3% yield; 99.0 area % purity by HPLC)

EXAMPLE 10

(Conversion of 8,14-Dihydrothebaine to Hydrocodone Base)

Water (745 g) is charged to a reaction vessel followed by 8,14-dihydrothebaine (250 g, 0.8 mol) and then concentrated hydrochloric acid (120 g). The resulting solution is heated to 75±5° C. and monitored for reaction completion by in-process HPLC analysis. On completion, the solution is cooled to room temperature during which solids precipitate out of the solution. Water (500 g) is added and the mixture is further cooled to 7±2° C. and then basified to pH 9-10 with aqueous sodium hydroxide solution while maintaining the batch temperature at <20° C. The resulting slurry is stirred for 1 h and then the product collected by filtration and washed with water.

The wet product is transferred into a vessel and ethanol (500 g) is charged. The mixture is heated to 75±3° C. and held for 1 h. The resulting solution is then cooled to 20±5° C. and then further cooled to −5±5° C. After holding the batch at this temperature range for 1 h, the batch is filtered and washed with ethanol pre-cooled to 0-2° C. (2×250 g). The product is dried at 55±5° C., under vacuum, to give Hydrocodone base (yield, 192.1 g, 80.4%; purity 99.8 area %).

EXAMPLE 11

(Conversion of Hydrocodone Base to Hydrocodone Bitartrate Hemipentahydrate)

Hydrocodone base (5 g, 0.017 mol) is charged with water (10 g) and ethanol (30 g) and the stirred mixture heated to 70° C. with complete dissolution of the solid occurring at approximately 60° C. A solution of L-(+)-tartaric acid (2.57 g, 0.017 mol, 1.02 equivalents) in water (10 g) and ethanol (30 g) is added to the reaction solution, while maintaining the batch temperature above 60° C. The resulting solution is held at 65-70° C. for 2 h then cooled over 1 h from 70° C. to 25° C., with vigorous stirring. Solid precipitated at approximately 45° C. The product slurry is cooled to 0° C., held for 1 h and then filtered. The product is washed with ethanol pre-cooled to 0° C. (61 g) and dried at 58° C. under vacuum for 24 h to give solid product (7.34 g; 99.97 area % purity).

A portion of the product (5.74 g) is hydrated under vacuum at 50-60° C. to give hydrocodone bitartrate hemipentahydrate,

EXAMPLE 12

(Conversion of Oripavine to 8,14-Dihydrooripavine)

Figure 2:
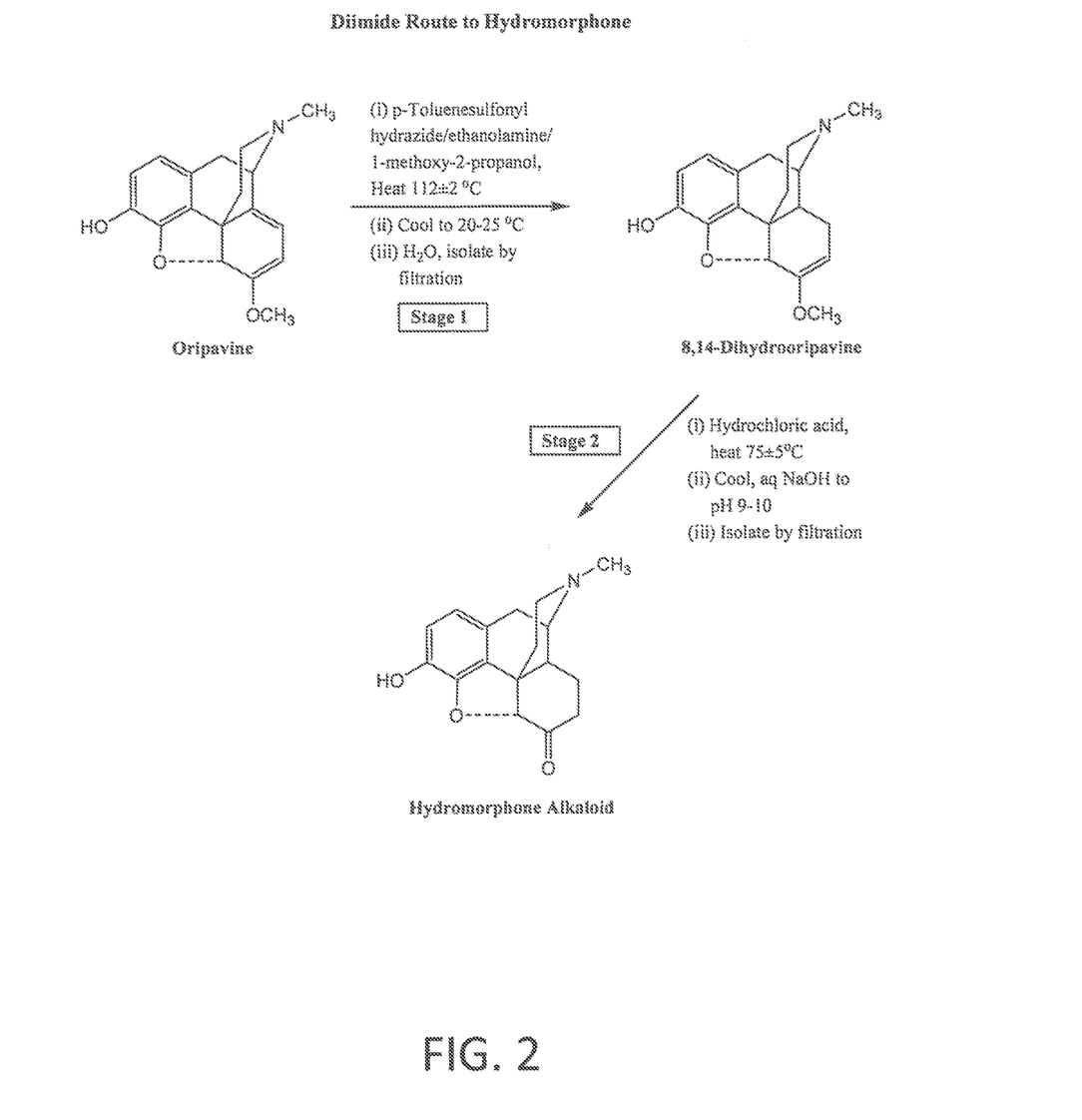
FIG. 2 is a schematic of a reaction of oripavine to hydromorphone alkaloid via 8,14-dihydrooripavine according to an embodiment of the present invention.

Oripavine (25.0 g containing ~20 wt % water, 20.0 g dry basis, 0.067 mol, 1.0 equiv) is placed in a mixture of 1-methoxy-2-propanol (65 g) and ethanolamine (6.8 g, 0.11 mol, 1.66 equiv) and is heated to 108±2° C. in a reaction vessel to give almost a complete solution. In another vessel, p-toluenesulfonylhydrazide (PTSH) (25.1 g, 0.134 mol, 2.0 equiv) is dissolved in a mixture of ethanolamine (50.0 g, 0.82 mol, 12.2 equiv) and 1-methoxy-2-propanol (4.2 g) at 20-25° C. The PTSH solution is then added slowly to the oripavine mixture at such a rate that the batch temperature remains in the range 108±2° C. and the gas evolution vents safely. After the complete addition, the reaction mixture is allowed to agitate at 108±2° C. and is monitored for reaction completion by in-process HPLC analysis. On completion, the batch is cooled to 15±5° C. Water (1200 g) is then charged to the batch while maintaining the batch temperature at ≤30° C. The resulting mixrure is stirred and the pH adjusted to 8-9 with acetic acid-water mixture. The batch is further cooled to 5±3° C. and held for a minimum of 1 hour. The product is collected by filtration, washed with water (3×40 g) and then dried at 55±5° C. to a constant weight to give 8,14-dihydrooropavine (14.2 g, 70.5% yield; 94.7 area % purity). On trituration with water the 94.7 area % purity of the product is increased to >97.5 area %.

The process described here in Example 12 is shown schematically in FIG. 2.

EXAMPLE 13

(Conversion of 8,14-Dihydrooripavine to Hydromorphone Base)

8,14-Dihydrooripavine (11.19 g; 0.037 mol) is charged with water (38 g) followed by concentrated hydrochloric acid (6.1 g). The resulting solution is heated to 75±5° C. and monitored for reaction completion by in-process HPLC analysis. On completion, the solution is cooled to room temperature and water (24 g) is added and the mixture further cooled to 7±2° C. and then basified to pH 9-10 with aqueous sodium hydroxide solution while maintaining the batch temperature at <20° C. The resulting slurry is stirred for 1 h and then the product collected by filtration, washed with water and dried.

The crude product is transferred into a vessel and ethanol (14g) is charged. The mixture is heated to 75±5° C., held for 1 h then cooled to 20±5° C. and further to −5±5° C. After holding at this temperature range for 1 h the batch was filtered and washed with ethanol pre-cooled to 0-2° C. (2×10 g). The product is dried at 55±5° C., under vacuum, to give Hydromorphone base (7.54 g, 70.7% yield; 99.8 area % purity).

We claim:

1. A process for preparing 8,14-dihydrothebaine, the process comprising the steps of:
    a. dissolving thebaine in an alkoxy solvent and, optionally, at least one first co-solvent to form a thebaine mixture;
    b. heating the thebaine mixture;
    c. separately dissolving a sulfonic acid hydrazide in an organic base and, optionally, a second co-solvent to form a hydrazide base solution; and
    d. adding the hydrazide base solution and the thebaine mixture at such a rate to maintain the temperature of the mixture to form a reaction mixture comprising 8,14-dihydrothebaine.

2. The process of claim 1, further comprising the step of cooling the reaction mixture to precipitate the 8,14-dihydrothebaine.

3. The process of claim 2, further comprising the step of adding water to the reaction mixture.

4. The process of claim 1, further comprising the step of triturating the 8,14-dihydrothebaine.

5. The process of claim 1, wherein the alkoxy solvent is an alkoxy alkanol or an alkoxy alkandiol.

6. The process of claim 5, wherein the alkoxy solvent is selected from the group consisting of 2-methoxyethanol, 2-ethoxyethanol, 2-propoxyethanol, 1-methoxy-2-propanol, 1-methoxy-2-butanol, 3-methoxy-1-butanol, 3-methoxy-3-methyl-1-butanol and 3-methoxy-1,2-propandiol.

7. The process of claim 1, wherein the first co-solvent is selected from the group consisting of ethanolamine, morpholine, ethylenediamine, and 1,3-propanediamine.

8. The process of claim 1, wherein the sulfonic acid hydrazide is p-toluenesulfonylhydrazide.

9. The process of claim 1, wherein the organic base is selected from the group consisting of ethanoamine, morpholine, ethylenediamine, and 1,3-propanediamine.

10. The process of claim 1, wherein the second co-solvent is an alkoxy alkanol or an alkoxy alkandiol.

11. The process of claim 1, wherein the thebaine mixture is heated to about 108±2°C.

12. The process of claim 1, wherein the amount of the sulfonic acid hydrazide is about 2 equivalents relative to the thebaine.

13. The process of claim 1, wherein the amount of the organic base is about 12equivalents relative to the thebaine.

14. The process of claim 1, wherein the reaction mixture pH is at least 9.5.

15. The process of claim 1, wherein the hydrazide base solution is continuously combined with the thebaine mixture.

16. The process of claim 1, wherein the hydrazide base solution is combined with the thebaine mixture at a steady rate.

17. A 8,14-dihydrothebaine composition wherein the product comprises less than about 0.1%, by HPLC, thebaine.

18. The product of claim 17, wherein the product has no detectable, by HPLC, sulfonic acid hydrazide impurities.

19. A process for making hydrocodone comprising the steps of:
    a. preparing 8,14-dihydrothebaine by the process of claim 1; and
    b. hydrolyzing the 8,14-dihydrothebaine to form hydrocodone.

20. A process for making a hydrocodone salt comprising the steps of:
    a. preparing 8,14-dihydrothebaine by the process of claim 1;
    b. hydrolyzing the 8,14-dihydrothebaine to form hydrocodone; and
    c. combining the hydrocodone with an acid to form a hydrocodone salt.

* * * * *